(12) United States Patent
Slaateng

(10) Patent No.: US 9,962,227 B2
(45) Date of Patent: May 8, 2018

(54) CONTAINER FOR DISPOSAL OF SOLID PHARMACEUTICALS AND A USE OF A CONTAINER

(71) Applicant: Lars Andre Slaateng, Bodö (NO)

(72) Inventor: Lars Andre Slaateng, Bodö (NO)

( * ) Notice: Subject to any disclaimer, the term of this patent is extended or adjusted under 35 U.S.C. 154(b) by 215 days.

(21) Appl. No.: 14/771,326

(22) PCT Filed: Feb. 28, 2014

(86) PCT No.: PCT/NO2014/050025
§ 371 (c)(1),
(2) Date: Aug. 28, 2015

(87) PCT Pub. No.: WO2014/133398
PCT Pub. Date: Sep. 4, 2014

(65) Prior Publication Data
US 2016/0000509 A1 Jan. 7, 2016

(30) Foreign Application Priority Data

Mar. 1, 2013 (NO) .................................. 20130310

(51) Int. Cl.
*B65D 1/24* (2006.01)
*A61B 19/02* (2006.01)
(Continued)

(52) U.S. Cl.
CPC .......... *A61B 19/0287* (2013.01); *A61B 50/36* (2016.02); *A61J 1/00* (2013.01);
(Continued)

(58) Field of Classification Search
CPC .... B65F 1/02; B65F 1/1615; B65F 2240/145; B09B 3/0075; A61J 1/03; A61J 1/00;
(Continued)

(56) References Cited

U.S. PATENT DOCUMENTS

| 4,494,652 A | 1/1985 | Nelson et al. |
| 4,541,765 A * | 9/1985 | Moore ................... B65D 88/62 |
| | | 220/1.6 |

(Continued)

FOREIGN PATENT DOCUMENTS

| EP | 2151210 A2 | 2/2010 |
| SE | 469521 B | 7/1993 |

(Continued)

OTHER PUBLICATIONS

Norwegian Search Report, dated Aug. 12, 2014, by Kjell Amundsen.
International Search Report and Written Opinion dated Jun. 10, 2014 (PCT/NO2014/050025).

*Primary Examiner* — Andrew R Kirsch
*Assistant Examiner* — Don M Anderson
(74) *Attorney, Agent, or Firm* — Alix, Yale & Ristas, LLP

(57) ABSTRACT

Container for disposal of solid pharmaceuticals and the like, comprising a receiving section and a disposal chamber. The receiving section comprises—a first member being hollow, having one opening outside of the container, and the other opening inside the container, and—a second member being inside the container, the second member is performed as a flexible tube connected to the receiving section in one end, and having the other end freely suspended above the disposal chamber. The first member is guiding solids thrown into the opening outside the container to the second member which guides the solids into the disposal chamber. The invention also concerns a use of a container of the above type.

20 Claims, 3 Drawing Sheets

(51) Int. Cl.
*A61J 1/00* (2006.01)
*B65D 25/04* (2006.01)
*A61B 50/36* (2016.01)
*B09B 3/00* (2006.01)
*B65F 1/02* (2006.01)
*B65F 1/16* (2006.01)

(52) U.S. Cl.
CPC ............ *B09B 3/0075* (2013.01); *B65D 25/04* (2013.01); *B65F 1/02* (2013.01); *B65F 1/1615* (2013.01); *B65F 2240/145* (2013.01)

(58) Field of Classification Search
CPC ........ B65D 25/04; B65D 51/24; B65D 11/08; A61B 50/36
USPC .... 220/501, 500, 505, 528, 553, 554, 908.3, 220/212, 601, 254.3, 254.1; 232/44, 43.1, 232/43.3; 141/286, 313, 320, 326, 331, 141/374, 382, 337, 345, 344
See application file for complete search history.

(56) References Cited

U.S. PATENT DOCUMENTS

| | | | |
|---|---|---|---|
| 4,576,281 A | 3/1986 | Kirksey | |
| 4,856,568 A * | 8/1989 | Murphy | ................... B67C 11/00 141/337 |
| 4,930,631 A | 6/1990 | Bruno | |
| 5,080,251 A | 1/1992 | Noack | |
| 5,127,522 A | 7/1992 | Ranford | |
| 5,419,435 A | 5/1995 | Perzan et al. | |
| 5,467,918 A * | 11/1995 | Glover | ..................... A45C 1/12 232/43.1 |
| 8,616,397 B2 * | 12/2013 | Maness | ................. B09B 3/0075 206/204 |
| 2002/0100706 A1 | 8/2002 | Sherman et al. | |
| 2005/0103662 A1 | 5/2005 | Iske et al. | |
| 2008/0217447 A1 | 9/2008 | Jeansonne et al. | |
| 2009/0294312 A1 | 12/2009 | Hitson | |
| 2011/0259467 A1 | 10/2011 | Maness | |
| 2012/0004761 A1 | 1/2012 | Madruga | |

FOREIGN PATENT DOCUMENTS

| | | |
|---|---|---|
| WO | WO2004011164 A2 | 2/2004 |
| WO | WO2011152839 A1 | 12/2011 |

\* cited by examiner

CONTAINER FOR DISPOSAL OF SOLID PHARMACEUTICALS AND A USE OF A CONTAINER

The present invention is related to a container for disposal of solid pharmaceuticals such as tablets, capsules and the like, according to the preamble of claim 1.

BACKGROUND

Medical practitioners, pharmacies, hospitals and other professional healthcare related services have stringent regulations regarding use and management of pharmaceutical products. This includes handling of surplus pharmaceuticals, among others pharmaceuticals signed out to a patient which the patient did not take, or pharmaceuticals which are out of date. Whenever stock-controlled drugs are disposed of, details regarding the relevant drug are entered in the drugs register, before disposal.

Disposed solid drugs are however, often accumulated in rather simple containers, typically produced of cardboard or plastic with a removable lid. All kinds of solid drugs are mixed into these containers, both nonprescription and prescription drugs. Theft or loss from these containers are not easily discovered, due to the easy access, the amount of mixed tablets, pills, capsules and the like in the container, and because the drugs are removed from all registers as they are disposed. Health care workers often consider this as a security break, and there is a mismatch between the levels of control of the drugs before and after they are disposed.

By "solid drugs" or "solid pharmaceuticals" it is meant all kinds of pharmaceuticals in solid form, such as, but not limited to tablets, pills, capsules (both plain and coated), ampulla, vials, sucking tablets, sweets, chewing gum, pessaries, vaginal tablets, suppositories as well as pellets and the like.

An object of the invention is to provide a closed container for safe disposal of solid pharmaceuticals, wherein the disadvantages mentioned above is avoided. Further, it should be difficult to remove pharmaceuticals being disposed in the container. Yet another object of the invention is that the container should be easy to label and cost-efficient to produce.

The objects above are fulfilled with a container according to the characterizing part of the independent patent claims.

DETAILS OF THE INVENTION

A container according to the present invention comprises a receiving section and a disposal chamber for accumulation of the disposed solid pharmaceuticals, wherein the receiving section is performed in a way allowing entrance to, but not exit from the chamber. It should not be possible to remove the solids being accumulated in the chamber through the receiving section, not even if the container is twisted, turned, shaken, poked or the similar. Further, it should not be possible to remove solids from the container even by applying vacuum or other forms of manipulation through the receiving section. Thus, a container according to the present invention enables a secure storage of all types of solid pharmaceuticals because these are deposited through a one-way entrance.

The receiving section of the container comprises two main members:
- a first member being hollow, and having one opening outside of the container, and the other opening inside the container, and
- a second member being inside the container, the second member is performed as a flexible tube connected to the receiving section in one end, and having the other end freely suspended above the disposal chamber.

The first member is guiding solids thrown into the opening outside the container to the second member which guides the solids into the disposal chamber.

In a preferred embodiment, the first member is performed as a pipe reaching through a wall of the container, or a pipe shaped part being integrated in a wall of the container. The opening of the first member being outside the container, must be higher than the opening inside the container, in such a way that the solid drugs fall through the member and into the container.

The first member is most preferred an integrated part of the top wall of the container, in order to utilize as much as possible of the container as disposal chamber. In another embodiment, the opening of the first member being outside of the container is shaped as a funnel, easing the entering of multiple solids at same time. In the most simple embodiment, the first member is just an opening in the top wall of the container, wherein the solids may be guided into the second member.

In a further preferred embodiment, the first member have at the least two baffles arranged inside the first member, each baffle should preferably cover at the least about half of the cross section of the first member, and should be horizontal or inclining towards the disposal chamber. Further, the baffles should be placed above/below and opposite each other, covering different parts of the cross section. In this way, solid pharmaceuticals thrown into the opening will be guided into the container, but the baffles will restrict the cross section in such a way that the passage will not be straight, and thus insertion of a wire or the similar to wriggle out pharmaceuticals will be prevented.

By "flexible tube" it is meant any tube shaped element, being sufficiently flexible to fold and thus close the passage therethrough. The flexible tube should preferably be of a material which is flexible, non-sticky and easily foldable, and yet strong enough to be suspended. The flexible tube may be performed in many ways and of many different materials, which will be obvious to a person skilled of the art. However, possible materials may be latex, silicone or a textile such as a tubular gauze bandage or the similar.

The second member should be connected to the receiving section in one end, and the other end should be freely suspended above the disposal chamber. The flexible tube is thus fastened only in the upper end, for instance to the first member. The other end of the flexible tube will thus be hanging above the disposal chamber, in such a way that any solid pharmaceuticals received in the second member will fall out of the free end and into the disposal chamber. The free end of the tube should move freely, and since the tube is made of a flexible and foldable material, the tube should close the passage in, or into the tube if the container is sufficiently tilted.

In a preferred embodiment, the flexible tube being the second member, has an reinforcement element at the free end of the tube, holding the free end of the tube open at all times. The reinforcement element may be an integrated part of the second member, such as a molded part, or it may be a separate part, fastened to the free end of the second member. The element should preferably be larger than the opening whereto the first end of the second member is fastened, in order to prevent that the second member can be taken out of the container, and thereby creating a possibility to wriggle out solids from the disposal chamber.

The reinforcement element at the end of the tube should be stiff enough to keep the tube end open, and heavy enough to keep a lower part of the tube in vertical direction, even when the container is twisted, tilted or turned. The material of the element and of the tube will depend on each other, which will be obvious for a person skilled of the art. If the material of the tube is tubular gauze, then the reinforcement element might be an o-ring of rubber, or a ring of plastic or metal.

In a preferred embodiment, the receiving section further comprises a third member, between the first and second member, inside the container. The third member has the form of a funnel where the larger opening is facing the first member, and the smaller opening is connected to the second member. Solids falling trough the first member will be collected in the funnel and guided into the second member. The third member may be fastened directly to the first member, or placed below it, in order to collect any solids falling through the first member. In a further preferred embodiment, the smaller opening of the funnel is not situated directly below the internal opening of the first member. In this way the passage through the receiving section is not a straight line, and thus insertion of any means for wriggling out disposed solid pharmaceuticals will be prevented.

When solids are put into the container, they fall down trough the first member, possibly guided by the baffles, and into the third or second member. If the container comprises a third member, the solids will fall from the internal opening of first member and into the funnel. One end of the second member is fastened to the outlet of the funnel, and the solids will be guided through the second member, passing the reinforcement element and falling into the disposal chamber. If the container does not comprise a third member, one end of the second member will be fastened to the internal opening of the first member, and the solids will fall directly from the first member to the second member. The container can only be filled until the solids no longer fall out of the second member.

If someone tries to get disposed solids out of the container by turning, tilting, shaking, poking or the similar, the second member, being the flexible tube, will bend and/or fold to one of the sides, and thus close the opening of the first or third member, or fold upon itself and close the passage therethrough. Even if one should succeed to balance the free opening of the second member with the opening of the first or third member, the reinforcement element of the second member will prevent the second member from coming out of the disposal chamber, and thus it is not possible to wriggle disposed solids out of the disposal chamber. The same will be the case if one tries to use vacuum to remove disposed solids through the opening. Further, the baffles of the first member, and possibly the lateral displacement of the internal opening of the first member and the narrower opening of the third member, will prevent insertion of something through the receiving section in order to keep the second member open while shaking, turning and/or poking the container.

A container according to the invention will thus make it difficult for anyone trying to get hold of disposed pharmaceutical solids, without destroying the container. In use, the containers will be labelled with control numbers, such as individual serial numbers. The containers themselves will be part of the control system and registers, and typically two authorized persons sign the label both when the container is taken in use, and when it is transferred for destruction. Thus, if the whole container is replaced or destroyed, it will be discovered. In this way, a container according to the invention will prevent theft of disposed pharmaceutical solids.

BRIEF DESCRIPTION OF THE DRAWINGS

In the following, the invention and some of its advantages will be described in detail, by reference to drawings of a preferred embodiment of a container. The drawings are given for illustration only, and show a non-limiting embodiment of the container, where.

DETAILED DESCRIPTION

Figure 1:
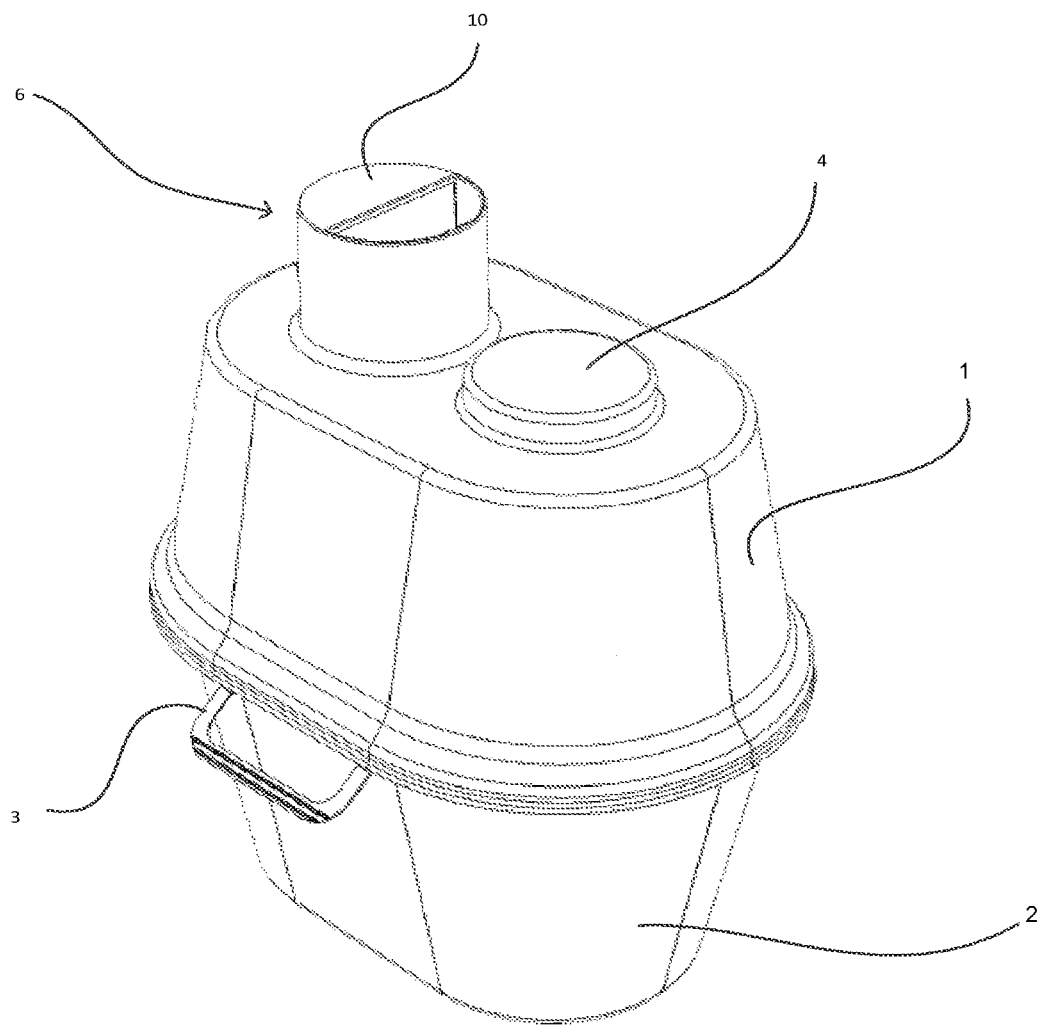
FIG. 1 shows a container according to the invention, seen in a perspective from the outside.

In the embodiment shown in the Figures, the container comprises a bottom, sidewalls and a top. It is molded in two parts 1, 2, both having an outwards flange, and the parts are fastened to each other in that flanges create a snap lock, but they could also be performed with threads. In order to avoid possible thefts, the parts must be securely fastened to each other, for instance by an adhesive or similar (not shown). The container may however, be manufactured in many ways, which will be obvious to a person skilled of the art.

Further, the shown container is provided with a handle 3 and a holder 4 for a possible lid for the entrance of the container. The lid may be placed on the entrance of the container for instance during transportation, preventing fluids from coming into the container. These parts can be performed in many ways, which will be obvious to a person skilled of the art, and thus they are not described any further.

The shown container comprises a disposal chamber 5 in the lower part, and the upper part of the container comprises a receiving section, having three main members;

a first member 6 being hollow and having one opening outside the top of the container, and the other opening inside the container, a third member being a funnel 7, where its upper, wider end is fastened to the inside of the container, where the sidewall meets the top wall, and a second member being performed as a flexible tube 8, wherein one end is fastened to the lower, narrower end of the funnel, and the other end is freely suspended above the disposal chamber 5.

The flexible tube 8 is suspended in one end, and is hanging freely above the disposal chamber. It has a reinforcement element 9 at the free end of the tube. The reinforcement element is stiff enough to hold the free end of the tube open at all times, and heavy enough to hold the tube vertically. Further, the cross section of the element 9 is larger than the cross section of the lower, narrower opening of the funnel 7, whereto the first end of the flexible tube is fastened, in order to prevent that the flexible tube 8 can be taken out of the container.

If the container is turned, twisted or tilted, the flexible tube will fold to one of the sides, and close the passage through the tube and/or the narrower outlet of the funnel. Thus, any waste in the disposal chamber can not get out through the receiving section.

In the shown embodiment, the first member is performed as a pipe, integrated in and raised above the top of the container. In this way it is possible to increase the available volume of the disposal chamber without increasing the size of the container. The first member 6 is further provided with two baffles 10, 11, one horizontal and one inclining towards the interior of the container. The baffles may, of course, be performed in many other ways, being obvious to a person skilled of the art.

Figure 2:
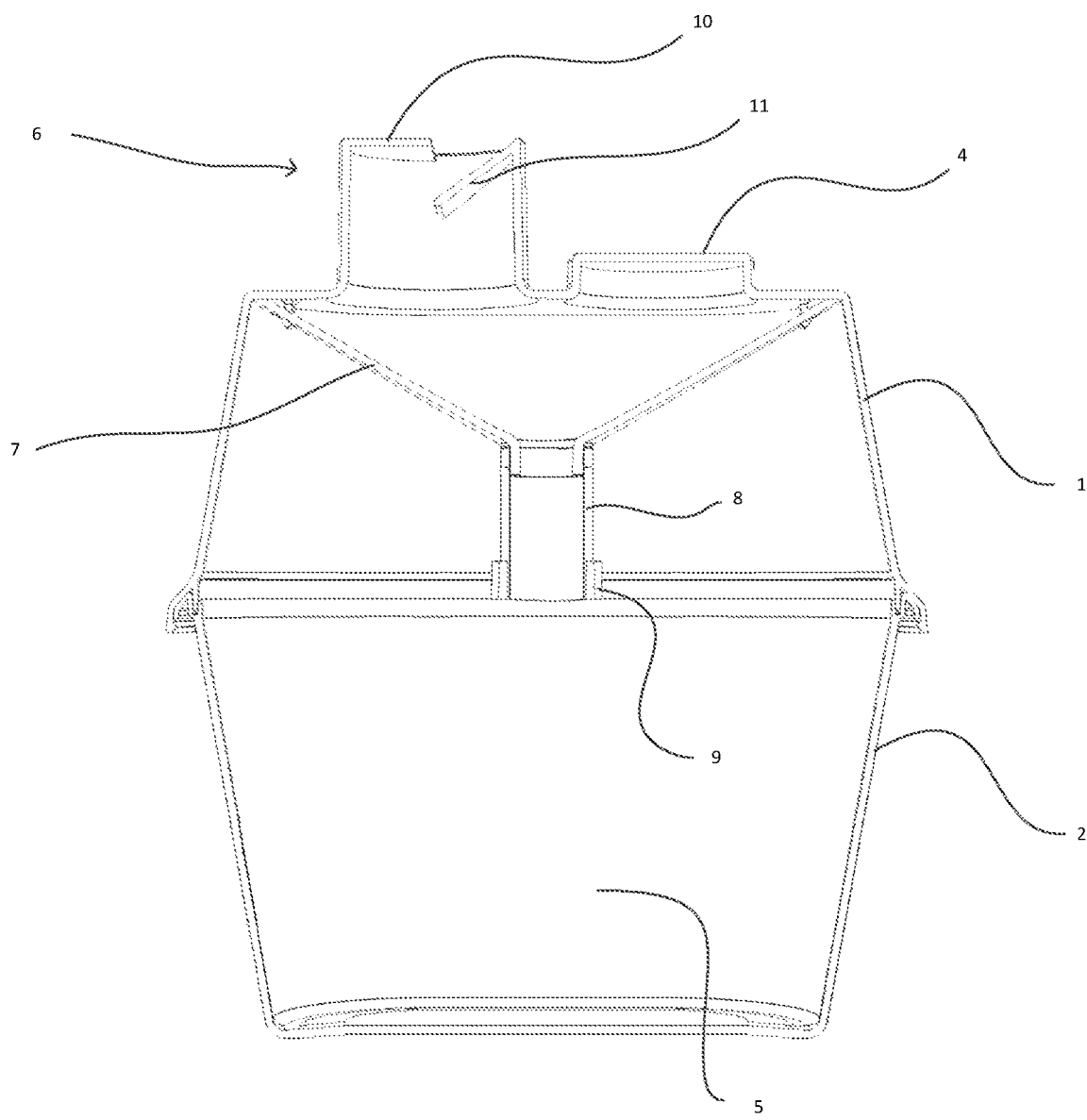
FIG. 2 shows a vertical cross section of the container in FIG. 1.
Figure 3:
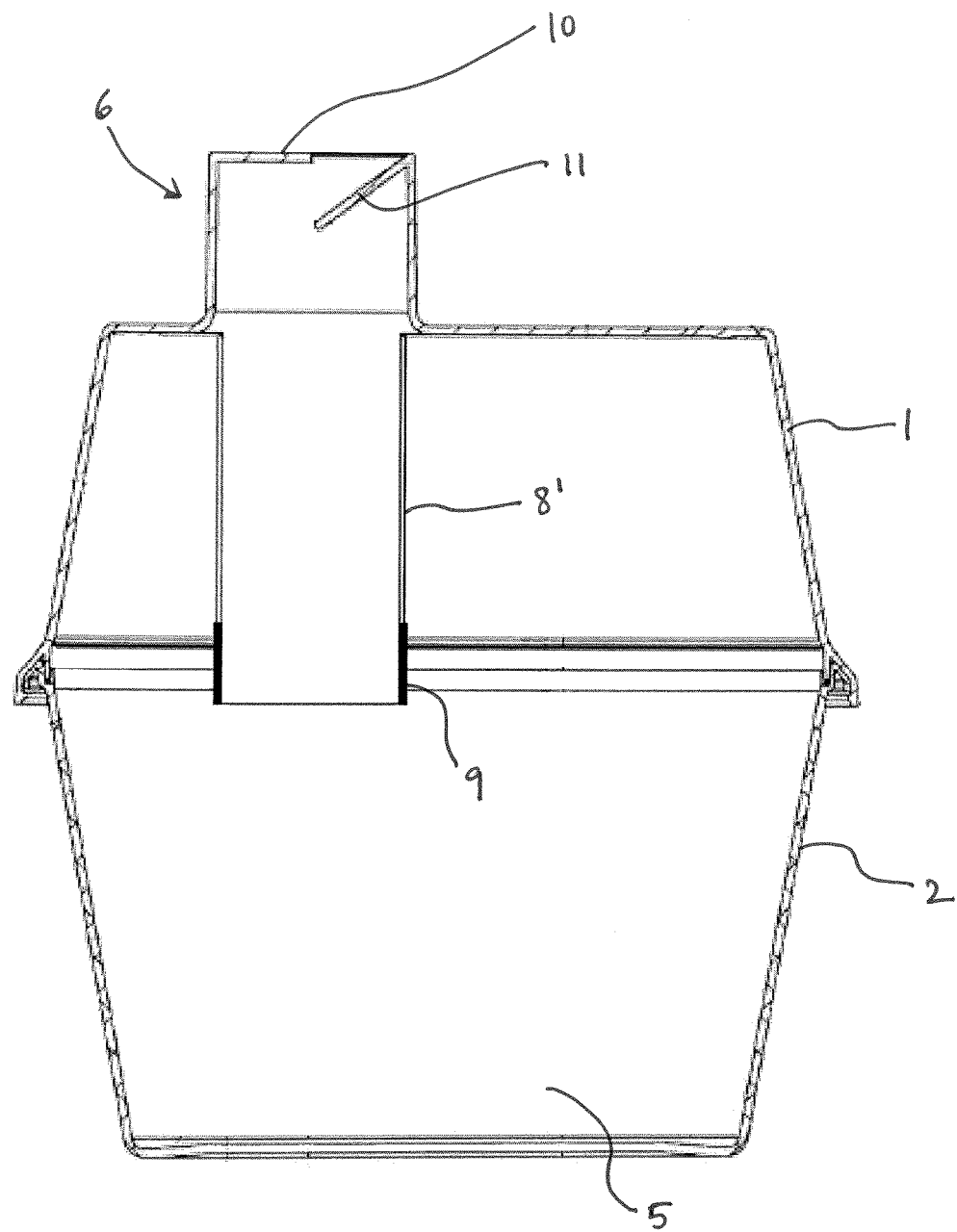
FIG. 3 shows another embodiment of the disclosed container.

FIG. 3 shows another embodiment of the disclosed container wherein the flexible tube 8' is connected directly to the first member 6 without an intermediate third member, like that depicted as reference numeral 7 in the FIG. 2 embodiment. As shown in FIG. 3, the remaining elements are identical to those of the FIG. 2 embodiment.

Although the invention has been described in the above in connection with preferred embodiments of the invention, it will be evident for a person skilled in the art that several modifications are conceivable without departing from the invention as defined by the following claims.

The invention claimed is:

1. Container for disposal of pharmaceutical solids, having a receiving section and a disposal chamber (5), wherein the receiving section comprises:
   a first hollow member (6), having one opening outside the container, and another opening inside the container, and
   a second member inside the container, in the form of a flexible tube (8) having opposite ends and defining a passage, with one end in communication with the first member, and the opposite end freely suspended above the disposal chamber,
   whereby the first member guides solids deposited into the opening outside the container to the second member which guides the solids into the disposal chamber (5), wherein the flexible tube folds to close the passage when the container is turned, twisted or tilted.

2. Container according to claim 1, wherein the first member is formed as a pipe (6) integrated with a wall of the container.

3. Container according to claim 1 wherein at least two baffles (10, 11) are arranged within the first member.

4. Container according to claim 3, wherein the first member is formed as a pipe, each baffle covers about half of the cross section of the first member, and leads towards the disposal chamber.

5. Container according to claim 4, wherein the pipe is vertically oriented and the baffles are above and opposite each other, covering different parts of the cross-section.

6. Container according to claim 1, wherein the flexible tube (8), has a reinforcement element (9) at the free end of the tube, holding the free end of the tube open.

7. Container according to claim 6, wherein the reinforcement element (9) is larger than an opening where one end of the tube (8) is fastened, thereby preventing the free end of the tube from being taken out of the container.

8. Container according to claim 1, wherein the flexible tube is of a non-sticky, easily foldable material.

9. Container according to claim 1, wherein the receiving section further comprises a third member (7), arranged between the first (6) and second member (8) through which the first member and second member communicate, and the third member has the form of a funnel in which a larger opening is facing up towards the first member, and a smaller opening is connected to the second member.

10. Container according to claim 9, wherein the third member is fastened directly to the first member.

11. Container according to claim 2, wherein at least two baffles (10, 11) are arranged within the first member.

12. Container according to claim 2, wherein the flexible tube (8), has a reinforcement element (9) at the free end of the tube, holding the free end of the tube open.

13. Container according to claim 8, wherein the material is a textile.

14. Container according to claim 8, wherein the material is latex.

15. Container according to claim 8, wherein the material is silicone.

16. Container according to claim 7, comprising a third member (7) positioned intermediate and operatively connected to the first member (6) and second member (8).

17. Container according to claim 16, wherein the third member (7) is substantially frustoconical in shape transitioning inward from a proximal end proximate the first member (6) toward a distal end proximate the second member (8).

18. Container according to claim 17, wherein the third member (7) includes a substantially cylindrical section at the distal end configured for engagement with one end of the second member (8).

19. A method of disposing of pharmaceutical solids, comprising depositing said solids into a container defined by claim 1.

20. The method of claim 19, comprising depositing said solids through at least two baffles arranged within the first member.

* * * * *